US00PP37699P2

(12) United States Plant Patent
Trees

(10) Patent No.: US PP37,699 P2
(45) Date of Patent: Sep. 15, 2026

(54) RASPBERRY PLANT NAMED 'SFF-20-015'

(50) Latin Name: *Rubus idaeus*
Varietal Denomination: SFF-20-015

(71) Applicant: Sunrise Farm Flowers, LLC, Arroyo Grande, CA (US)

(72) Inventor: Scott C Trees, Arroyo Grande, CA (US)

(73) Assignee: Sunrise Farm Flowers, LLC, Arroyo Grande, CA (US)

( * ) Notice: Subject to any disclaimer, the term of this patent is extended or adjusted under 35 U.S.C. 154(b) by 0 days.

(21) Appl. No.: 19/436,296

(22) Filed: Dec. 30, 2025

(51) Int. Cl.
*A01H 5/08* (2018.01)

(52) U.S. Cl.
USPC ..... Plt./204

(58) Field of Classification Search
USPC ..... Plt./156, 203, 204
See application file for complete search history.

(56) References Cited

U.S. PATENT DOCUMENTS

PP35,903 P2 * 7/2024 Vitten ..... Plt./204

* cited by examiner

*Primary Examiner* — Karen M Redden
(74) *Attorney, Agent, or Firm* — Weatherly IP Solutions, LLC; Karen P. Bechtold; James M. Weatherly

(57) ABSTRACT

A new variety of Raspberry plant named 'SFF-20-015' which bears fruit on its current season's growth spineless primocanes on a vase-shaped shrubby plant habit. 'SFF-20-015' flowers without requirement for vernalization and bears yellow-bronze colored berries which are very sweet. 'SFF-20-015' is an easily grown fruiting raspberry plant for the home gardener market.

2 Drawing Sheets

Genus and species: *Rubus idaeus*.
Variety denomination: 'SFF-20-015'.

BACKGROUND

The present disclosure relates to a new and distinct cultivar of Raspberry. Although the instant variety is known botanically as *Rubus*, it is described herein as Raspberry Plant named 'SFF-20-015'.

Raspberries are commonly grown for commercial and home garden fruit production and are distinguished by their ability only to bear fruit on the basal shoots (also known as "canes") which arose and matured during the previous growing year. In recent years, hybridizers have developed and released varieties of Raspberry whose current season's growth of basal shoots will bear fruit later in the same year. Varieties which fruit on previous years' cane growth are termed "Floricane" varieties, and more recent hybrids which fruit on the current season's canes are termed "Primocane" varieties. The instant variety 'SFF-20-015' is a Primocane Variety which had been developed as an easily grown fruiting shrub for the home gardener market, allowing home gardeners to avoid the requirement of Floricane varieties to be trained on canes or trellises, then pruned in late summer and be trained in the second season to grow upright for harvesting of fruit in the second year.

'SFF-20-015' originated and was selected from a Raspberry breeding program which was started in January 2014 in Arroyo Grande, California. Plants of the yellow-fruited Primocane Raspberry Plant Named 'Anne' (U.S. Plant Pat. No. 10,411) were grown in the greenhouse and in the field for exposure to open pollination by unknown male Raspberry plants. Ripe fruit was harvested during the growing season 2014 from which seeds were extracted processed for storage and for germination. In 2015, several hundred seedlings were planted in the field and observed for earliness to flower, compact branched habit, spineless (or nearly spineless canes). After growing out to mature size, and observing for two years, spineless, yellow-fruited plants were identified and asexually propagated them for further trials and observation. In spring 2020, two yellow-fruited seedlings were identified which had maintained a dwarf habit and continuous Primocane fruiting without any winter chilling requirement. Of the two seedlings, the instant variety was selected for better and sweeter flavor and was identified as 'SFF-20-015'.

'SFF-20-015' was first asexually propagated in 2016 in Guadalupe, California. Internodal stem cuttings were rooted in commercial rooting medium. The cuttings were tented to maintain humidity while rooting. Rooting was complete after 21 days at ambient air and medium temperatures in the range 18 °C and 24 °C.

'SFF-20-015' is a stable Primocane variety of Raspberry which reproduces and grows and fruits true to type in successive generations of asexual reproduction.

SUMMARY

The following traits have been repeatedly observed and represent the distinguishing characteristics of 'SFF-20-015'. 'SFF-20-015' has not been tested under all possible conditions and phenotypic differences may be observed with variations in environmental, climatic, and cultural conditions, without however, any variance in genotype.

1. Short internode spineless primocanes.
2. Compact domed shrubby habit.
3. Flowering without requirement for vernalization.
4. Yellow-bronze colored fruit and fruit juice.

5. Pleasant fruit flavor with characteristic raspberry tartness combined with high sweetness.

DESCRIPTION OF THE PHOTOGRAPHS

The accompanying color photographs illustrate the overall appearance of the new Raspberry cultivar 'SFF-20-015' showing the colors as true as it is reasonably possible to obtain in colored reproductions of this type. Photographs were taken in summer 2020 in Santa Barbara, California from an eleven month old plant grown outdoors in a 2-gallon container, without any pruning or the use of any chemical growth regulators. Colors in the photographs may differ from the color values cited in the detailed botanical description, which accurately describes the actual colors of the new variety 'SFF-20-015'.

DESCRIPTION OF THE NEW VARIETY

Figure 1:
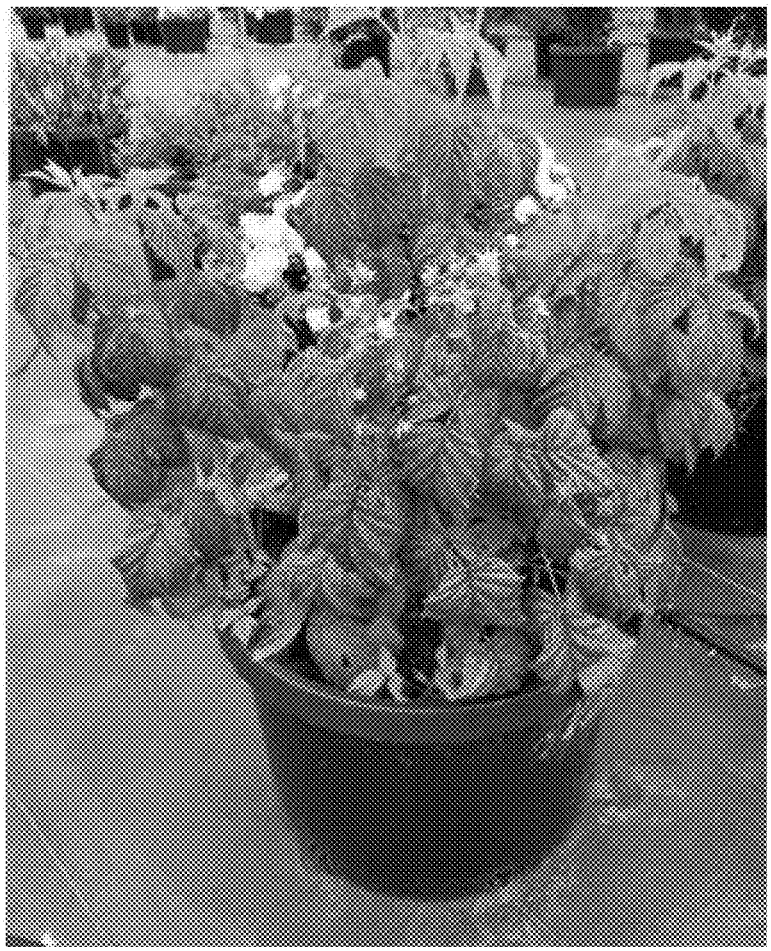
FIG. 1 depicts an entire plant in flower of 'SFF-20-015'.
Figure 2:
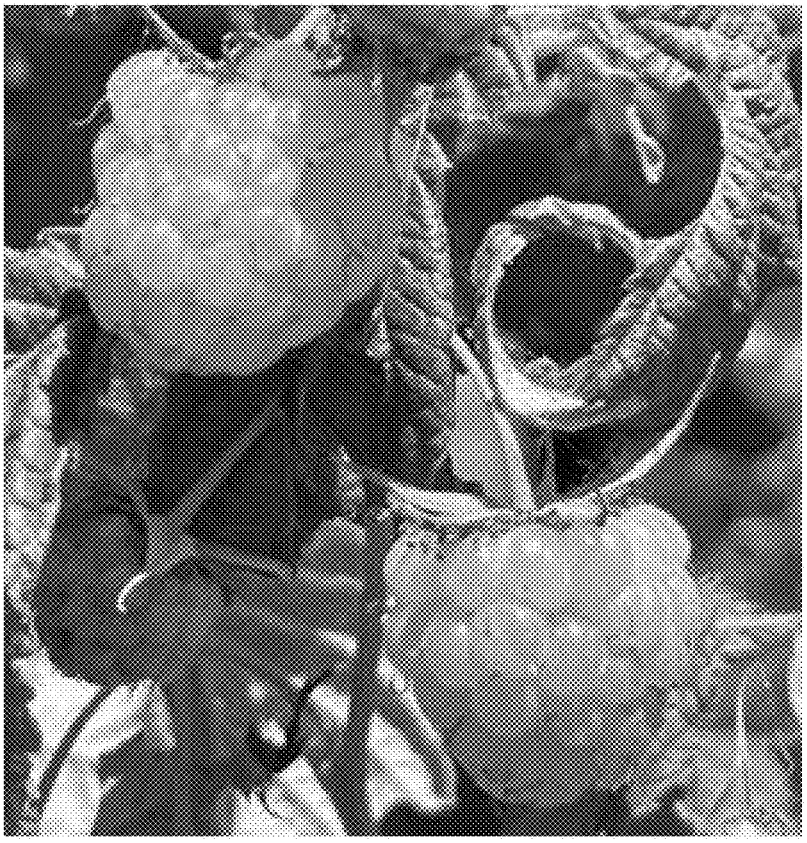
FIG. 2 depicts a close-up view of the fruit (berries) of 'SFF-20-015'.

The following detailed descriptions set forth the distinctive characteristics of 'SFF-20-015'. Observations, measurements, values, and comparisons were collected in Santa Barbara, California from two mature fruiting plants which had been grown outdoors in full sun in a 10-gallon container. The observed plants had been planted in Week 45 (early November) 2024 as clump divisions of the Inventor's selections. Color determinations were made in accordance with The 2007 Royal Horticultural Society Colour Chart from London England, except where general color terms of ordinary dictionary significance are used.

Classification:
- *Family*.—Rosaceae.
- *Genus*.—*Rubus*.
- *Species*.—Hybrid.
- *Common name*.—Raspberry.

Parentage:
- *Female parent*.—Raspberry Plant Named 'Anne' (U.S. Plant Pat. No. 10,411).
- *Male parent*.—Unknown.

Plant:
- *Type*.—Ornamental fruiting shrub.
- *Vigor*.—Prolific production of slender basal shoots (canes) with short internodes.
- *Habit*.—Upright vase-shaped.
- *Plant dimensions* (*established in* 10-*gallon container for* 10 *months*).—48 cm in height, 45 cm in diameter.
- *Hardiness*.—Hardy in the USDA Zone 10.
- *Root system type*.—Fine and fibrous with most roots concentrated in the uppermost 30 cm to 45 cm of the growing medium. Roots bear buds from which each new season's canes emerge.
- *Root color*.—Light brown to dark brown, ranging between RHS 177A and RHS N199B.
- *Recommended soil and growing conditions*.—Plant in a good mixture of well-draining sandy loam soil and avoid waterlogging.
- *Recommended light conditions* (*sun, shade*).—Full sun.
- *Crop time*.—8 months to fill out a 2 gallon container, 10 months to first fruiting in a 5 gallon container or larger.
- *Seasonal interest*.—Flowers produced continuously from early summer until late summer. Fruit produced and visible in July and August (peak fruiting). Some flowers are produced in late summer and fruiting may continue into fall.
- *What method used for propagation*.—Softwood cuttings or division of rooted plant.
- *Time to initiate roots*.—12 days.
- *Heat and humidity tolerance*.—Very well adapted to the heat and drought conditions.

Basal stems (primocanes):
- *Number per plant*.—7.
- *Number of fruiting canes*.—4.
- *Number of non-fruiting canes*.—3.
- *Cane shape*.—Round.
- *Cane dimensions*.—37 cm in length, 5 mm in diameter towards base, 2.5 mm in diameter towards apex.
- *Branching*.—None. Basal canes only.
- *Internode length* (*lower section towards base*).—2 cm.
- *Internode length* (*mid-section*).—2.5 cm.
- *Internode length* (*above mid-section to apex*).—1 cm.
- *Cane surface color*.—RHS 145D.
- *Cane anthocyanin*.—None.
- *Cane surface texture*.—Glabrous and smooth except where spined.

Spines:
- *Present or absent*.—Present.
- *Description*.—Hair-like, facing downwards (towards base of cane), wiry to semi-rigid.
- *Dimensions*.—1 mm to 2 mm in length, 0.5 mm in diameter at cane attachment.
- *Color*.—RHS 145D.
- *Arrangement*.—Encircling canes, more dense along stem upper surface.
- *Density*.—5 spines per 1 cm of cane length.
- *Color*.—RHS 145D.

Foliage, leaves:
- *Type*.—Deciduous, compound trifoliate consisting of large petiolate (rachis) terminal leaflet above two opposite sessile leaflets, forming a pair.
- *Arrangement*.—Compound leaves borne alternately on petioles.
- *Compound leaf attachment*.—Petiolate.
- *Compound leaf aspect*.—Upward facing towards apex.

Entire compound leaf:
- *Shape*.—Deltoid.
- *Apex* (*i.e. apex of terminal leaflet*).—Acute.
- *Base* (*i.e. base of lower sessile leaflet pair*).—Obtuse.
- *Dimensions overall*.—9 cm in length, 10.5 cm in width across lateral leaf pair.
- *Attachment*.—Petiolate (from stem to base of lower lateral leaflet pair).

Terminal leaflet:
- *Terminal leaflet shape*.—Deltoid.
- *Terminal leaflet division*.—Simple.
- *Terminal leaflet base*.—Cordate.
- *Terminal leaflet apex*.—Acute.
- *Terminal leaflet surface* (*adaxial surface*).—Rugose.
- *Terminal leaflet surface* (*abaxial surface*).—Matte, lightly pubescent.
- *Terminal leaflet color* (*leaflet fully expanded, adaxial surface*).—RHS 141A.
- *Terminal leaflet color* (*leaflet fully expanded*), *abaxial surface*).—RHS 191C.
- *Terminal leaf venation*.—Pinnate.
- *Terminal leaflet vein color* (*adaxial surfaces*).—RHS 151C.

*Terminal leaflet vein color* (*abaxial surface*).—RHS 145C.
*Terminal leaflet vein aspect* (*raised or depressed*).—Raised.
*Terminal leaflet dimensions*.—6.5 cm in length (base to apex), 4 cm in width.
*Terminal leaflet margins*.—Dentate, average of 3 teeth per 1 cm of margin length.
*Terminal leaflet margin teeth protrusion*.—2.5 mm.
*Terminal leaflet margin teeth apex*.—Acute, occasionally acuminate.
*Terminal leaflet attachment*.—Petiolate (rachis) between base of terminal leaflet and base of lateral leaflet pair.
*Rachis shape*.—Round, slightly sulcate facing upwards.
*Rachis color*.—RHS 151A.
*Rachis dimensions*.—20 mm in length, 1.5 mm to 2 mm in width.
*Rachis anthocyanin*.—Present on solar-facing upper surface, color RHS N34B.

Lateral leaflets:
*Lateral leaflet shape*.—Elliptic.
*Lateral leaflet division*.—Simple.
*Lateral leaflet shape*.—Adaxial surface convex, abaxial surface concave.
*Lateral leaflet dimensions* (*each leaflet*).—8 cm in length, 4.5 cm in width.
*Lateral leaflet base*.—Obtuse.
*Lateral leaflet apex*.—Acute.
*Lateral leaflet surface* (*adaxial*).—Rugose, leaf surface raised 2.5 mm between veins.
*Lateral leaflet surface* (*abaxial*).—Concave between veins, smooth, matte.
*Lateral leaflet venation*.—Pinnate.
*Lateral leaflet color* (*leaflet fully expanded, adaxial surface*).—RHS 141A.
*Lateral leaflet color* (*leaflet fully expanded, abaxial surface*).—RHS 191C.
*Terminal leaflet margins*.—Dentate, 3 deltoid teeth per 1 cm of margin length.
*Margin teeth apex*.—Acute.
*Lateral leaflet attachment*.—Sessile, opposite leaflet bases adjoin compound leaf petiole.

Petiole (compound leaf, from stem to base of lateral leaflet pair):
*Petiole shape*.—Round.
*Dimensions*.—2 cm in length, 1.5 mm in diameter.
*Strength*.—Stiffly firm, resists bending in any direction.
*Surface*.—Smooth, glabrous, spineless.
*Color*.—RHS 151A.
*Anthocyanin*.—None.

Peduncle:
*Shape*.—Round.
*Dimensions*.—Length, from uppermost leaf node to base of inflorescence): 18 mm. Diameter: 2 mm.
*Surface*.—Smooth, glabrous, spineless.
*Color*.—RHS 147C.
*Peduncle anthocyanin*.—Absent.

Inflorescence:
*Inflorescence type*.—Panicle.
*Quantity of inflorescences per plant*.—7 to 10.
*Dimensions*.—14 cm in length, including peduncle, 14 cm in width.
*Persistent or self-cleaning*.—Persistent. Inflorescence remains on plant as flowers senesce and self-clean. Inflorescence remains on plant as fruits fall away if not harvested.

Flowers:
*Quantity of flowers per inflorescence*.—10, including 7 large or small buds.
*Flower size* (*largest terminal flower in uppermost panicle*).—Flower height: 8 mm from sepal base to flat-topped apex of stamen cluster pillar in height. Flower diameter: 10 mm across fully-opened sepals.
*Flower size* (*smallest flowers on lowermost panicles*).—5 mm in height, 6 mm in diameter.
*Flowers persistent or self-cleaning*.—Self-cleaning.
*Flowers aspect*.—Facing upward and outward.
*Flower* (*petals*) *arrangement*.—Rotate.
*Flower shape, including open calyx and cluster of exserted stamens*.—Truncated cone.
*Flower fragrance*.—None.
*Flower lastingness*.—Petals remain on flowers (initially held vertically, later horizontally) for 8 to 10 days prior to falling away.

Petals:
*Number of petals per flower*.—4 to 5.
*Petals fused or unfused*.—Unfused.
*Petal shape*.—Spatulate.
*Petal dimensions*.—8 mm in length, 4 mm in width.
*Petal color* (*adaxial surface*).—RHS 155D.
*Petal color* (*abaxial surface*).—RHS 155D with feint longitudinal parallel light gray veins, color RHS 197D.
*Petal surface texture*.—Glabrous (both surfaces).
*Petal appearance*.—Semi-lustrous, especially adaxial surfaces.
*Petal margin*.—Smooth, entire except minutely dentate towards apex.
*Petal apex shape*.—Rounded, minutely crenate.
*Petal base shape*.—Truncate.

Calyx, sepals:
*Calyx dimensions* (*stamens fully open*).—5 mm in height, 30 mm in diameter.
*Sepal quantity*.—5.
*Sepals fused or unfused*.—Fused at base only.
*Sepal shape*.—Lanceolate, longitudinally undulating.
*Sepal apex shape*.—Acuminate, tiny spine approximately 5 mm in length, spine color RHS N200A.
*Sepal base shape*.—Truncate.
*Sepal dimensions*.—Length 11 mm, width 4.5 mm at base.
*Sepal color*.—(Adaxial surface): RHS 193A.
*Sepal color* (*abaxial surface*).—RHS 143C.
*Sepal surfaces* (*both surfaces*).—Lightly pubescent.
*Sepal margin*.—Smooth, entire, lightly colored band extending inward for 1.5 mm, color ranging between RHS NN155A and RHS 145D.
*Sepal surface*.—Faintly pubescent.

Pedicels:
*Shape*.—Round.
*Dimensions* (*average*).—15 mm in length, 2 mm in diameter.
*Surface texture* (*both surfaces*).—Smooth, semi-glossy.
*Color*.—RHS 144B.
*Anthocyanin*.—None.

Bud:
*Quantity of buds per inflorescence*.—7 large or small buds.
*Bud shape*.—Conical with rounded base, acute apex.
*Bud dimensions*.—6 mm in length, 5 mm in diameter.
*Bud color*.—RHS 144B.
*Surface*.—Shallow longitudinal ridges from base to apex, ridge color RHS 147C.

Reproductive organs:
*Stamens*.—Filaments: Quantity: 35 to 40. Arrangement: Filaments held upright in a tight flat-topped cylindrical cluster. Filaments: 4.5 mm in length, 0.5 mm in diameter. Filament color: RHS 155C.

*Anthers*.—Shape: Ovoid. Attachment: Central. Dimensions: 1 mm in length, 0.5 mm in diameter. Color: RHS N199B.

*Pollen*.—Absent on observed plants.

*Pistils*.—Quantity: 45 to 55. Dimensions: 5 mm to 6 mm in length, thin and slender, 0.25 mm in diameter. Color: RHS NN155D.

*Ovaries* (*observed immature only*).—After pollination, each ovary begins to swell and develop into a small, single-seeded fruit called a drupelet, each containing one seed. Ovaries position: Superior as swelling at base of pistil and attached to receptacle. Dimensions: 1 mm to 3 mm in length, 1.5 mm in diameter. Color: RHS 155C.

Fruit: The fruits of raspberry plants are commonly described as berries. Each berry is comprised of a number of small individual drupes or drupelets which developed as ripened ovaries. The drupelets contain the seeds within sweet gelatinous flesh. The drupelets are held tightly together forming an aggregate fruit.

Drupes (drupelets):

*Drupelet shape*.—Kernel shape, keeled underside.

*Drupelet quantity*.—50 to 60.

*Drupelet dimensions*.—4 mm in height above plane of adjacent drupes. 3 mm in height when detached, 4 mm to 6 mm in width.

*Drupelet firmness*.—Firm immature, soft, easily burst when fully ripened.

*Drupe color* (*first coloring, early season*).—RHS 4D.

*Drupe color* (*mid-season*).—RHS 14C.

*Drupelet color* (*most ripe, mid and late season*).—RHS 21C.

Seeds:

*Quantity*.—50 to 60 (1 seed per drupe).

*Location*.—Central within drupe.

*Shape*.—Ovoid.

*Dimensions*.—1.25 mm min length, 0.5 mm in diameter across center.

*Surface*.—Glossy membrane, matte when dried.

*Color* (*immature, membranaceous*).—RHS 159C.

*Color* (*dried*).—RHS 26B.

Berries (aggregate of drupelets):

*Berry shape*.—Oblique conical.

*Berry dimensions* (*maximum, fully developed and ripened*).—23 mm in height, 21 mm in diameter.

*Berry quantity*.—In total, 6 or 7 per inflorescence, including immature berries.

*Berry quantity* (*ripe, edible berries at one time peak harvest*).—At most, 2 per inflorescence.

*Berry yield per plant* (*ripe, edible berries*).—15 to 18 harvested over 3-week period.

*Berry ease of picking*.—Readily and lightly detaches from receptacle. Otherwise, berries will self-detach from receptacle and fall to the ground.

*Berry taste*.—Characteristic raspberry tartness combined with high sweetness.

*Juice sweetness* (*brix value*).—10.

*Berry hairs* (*withered pistils*).—Description: After pollination, the pistils of the flowers wither and constrict and remain affixed to the ovaries as they become drupes. These hairs remain as the drupes develop and ripen and are visible protruding between the drupes. Hair dimensions: 3 mm in length, very fine and wiry, width less than 0.25 mm. Hair color: RHS N200A.

*Berry trichomes*.—In common with raspberry berries generally, the drupes bear numerous many tiny very fine grey hairs (trichomes) which provide a defense against moisture, disease and insects. Trichome dimensions (protruding above the berry surface): 2 mm in length, width too small to measure, color RHS 156D.

Fruit characteristics:

*Weight* (*average of* 4 *berries*).—2.0 g.

*Berry surface color*.—Ranges between RHS 19A and RHS 20A.

*Juice color*.—RHS 11B, translucent.

*Sweetness*.—10 (Brix).

Receptacle: The berry receptacle (core or plug) remains on the plant after berry picking or after a berry natural falls away leaving a cavity inside the berry.

*Receptacle shape*.—Oblique conical, basal shoulder, rounded apex,

*Receptacle dimensions*.—Length (shoulder to apex): 12 mm. Diameter (shoulder): 12 mm.

*Receptacle color*.—RHS 145C becoming lighter RHS 11D towards apex, at berry center.

*Receptacle surface*.—Rough, dimpled.

Pest susceptibility: Slightly susceptible to grazing by caterpillars.

Disease susceptibility: None observed.

Heat, humidity and drought tolerance: Very well adapted to heat and drought conditions.

COMPARISON WITH PARENT

'SFF-20-015' is distinguished from its female parent variety Raspberry 'Anne' (U.S. Plant Pat. No. 10,411) as follows:

| | 'SFF-20-015' | Female Parent: 'Anne' (U.S. Plant Pat. No. 10,411) |
|---|---|---|
| Number of canes and suckering | Less than 10 short basal canes without suckering | More than 10 suckering canes |
| Fruit Color | Medium yellow when fully ripened | Golden yellow, tending to yellow-orange in color when fully ripened |
| Fruit Size | Larger than 'Anne' in both height (23 mm) and diameter (21 mm) | Smaller than 'SFF-20-015' in height (19 mm) and diameter (19 mm) |

COMPARISON WITH OTHER VARIETIES IN COMMERCE

'SFF-20-015' is distinguished from Commercial Raspberry variety 'Shortcake Red', which is also known as 'NR7' (U.S. Plant Pat. No. 22,141) as follows:

| | 'SFF-20-015' | 'Shortcake Red' ('NR7' - U.S. Plant Pat. No. 22,141) |
|---|---|---|
| Variety type | Primocane | Floricane |
| Fruit color | Medium-dark red | Medium-light pink |

I claim:

1. A new and distinct variety of Raspberry plant named 'SFF-20-015' as shown and described herein.

* * * * *